(12) United States Patent
Lebing et al.

(10) Patent No.: US 9,023,797 B2
(45) Date of Patent: May 5, 2015

(54) CAPRYLATE VIRAL DEACTIVATION

(71) Applicants: Wytold Lebing, Seattle, WA (US); Doug Burns, Raleigh, NC (US); Nathan Roth, Holly Springs, NC (US); Joann Hotta, Raleigh, NC (US)

(72) Inventors: Wytold Lebing, Seattle, WA (US); Doug Burns, Raleigh, NC (US); Nathan Roth, Holly Springs, NC (US); Joann Hotta, Raleigh, NC (US)

(73) Assignee: Grifols, S.A., Barcelona (ES)

( * ) Notice: Subject to any disclaimer, the term of this patent is extended or adjusted under 35 U.S.C. 154(b) by 0 days.

(21) Appl. No.: 13/951,070

(22) Filed: Jul. 25, 2013

(65) Prior Publication Data

US 2014/0163101 A1  Jun. 12, 2014

Related U.S. Application Data

(60) Provisional application No. 61/681,265, filed on Aug. 9, 2012.

(51) Int. Cl.
| | |
|---|---|
| *A61K 38/38* | (2006.01) |
| *C07K 14/76* | (2006.01) |
| *A01N 37/02* | (2006.01) |
| *C12N 7/00* | (2006.01) |

(52) U.S. Cl.
CPC ........ *A01N 37/02* (2013.01); *C12N 7/00* (2013.01); *C12N 2760/20263* (2013.01); *C12N 2770/24363* (2013.01); *C07K 14/76* (2013.01)

(58) Field of Classification Search
CPC .... C07K 14/765; C07K 14/76; C07K 16/065; A61K 38/38; A61K 35/16; A61K 39/292
See application file for complete search history.

(56) References Cited

U.S. PATENT DOCUMENTS 5,886,154 A * 3/1999 Lebing et al. ............ 530/390.1
5,986,062 A * 11/1999 Ohmura et al. ............ 530/363

FOREIGN PATENT DOCUMENTS

| EP | 0 696 595 A1 | 2/1996 |
| EP | 1 479 393 A1 | 11/2004 |
| WO | WO 98/24485 | 6/1998 |
| WO | WO0056768 A3 * | 9/2000 |
| WO | WO 2005/014648 A1 | 2/2005 |
| WO | WO 2005/082937 A2 | 9/2005 |

OTHER PUBLICATIONS

European Search Report Dated Sep. 24, 2013 in Corresponding European Patent Application No. 13177014.1.
First Examination Report dated Jul. 26, 2013 in corresponding New Zealand Patent application No. 613554.
Further Examination Report dated Sep. 5, 2013 in corresponding New Zealand Patent application No. 613554.
Johnston et al, "Low pH, Caprylate Incubation as a Second Viral Inactivation Step in the Manufacture of Albumin Parametric and Validation Studies", Biologicals, Academic Press Ltd., London, Gb, vol. 31, No. 3, Sep. 1, 2003, pp. 213-221, XP001149490.
Korneyeva et al, "Enveloped Virus Inactivation by Caprylate: A Robust Alternative to Solvent-Detergent Treatment in Plasma Derived Intermediates", Biologicals, Academic Press Ltd., London, Gb, 1-26, vol. 30, No. 2, Jun. 1, 2002, pp. 153-162, XP001197368.
Mpandi et al, "Partitioning and Inactivation of Viruses by the Caprylic Acid Precipitation Followed by a Terminal Pasteurization in the Manufacturing Process of Horse Immunoglobulins", Biologicals, Academic Press Ltd., London, Gb, vol. 35, No. 4, Oct. 1, 2007, pp. 335-341, XP022300726.

* cited by examiner

*Primary Examiner* — James H Alstrum Acevedo
*Assistant Examiner* — Jeanette Lieb
(74) *Attorney, Agent, or Firm* — RatnerPrestia (57) ABSTRACT

Described herein are methods for inactivating viruses using caprylate in solutions containing albumin.

21 Claims, 7 Drawing Sheets

FIG. 5A
LRV_0-100_Scale

Caprylate = 30.0
Temperature = 40.0

| Protein = 5.00 | | pH = 4.41 |
|---|---|---|
| Value | Low Limit | High Limit |
| 100.00 | 82.01 | 100.00 |

FIG. 5B
LRV_0-100_Scale

Caprylate = 30.0
Temperature = 40.0

CAPRYLATE VIRAL DEACTIVATION

CROSS REFERENCE TO RELATED APPLICATIONS

This application is a non-provisional of U.S. Provisional Application No. 61/681,265, filed on Aug. 9, 2012, the contents of which are herein incorporated by reference in its entirety.

TECHNICAL FIELD

Described herein are methods for inactivating viruses using caprylate during the purification of albumin from plasma.

BACKGROUND

Human serum albumin (hereafter albumin) is the most abundant protein in human blood plasma. Circulating albumin is a 585 amino acid protein with a molecular weight of 67 kDa. The protein has a serum half-life of about 20 days and is involved in transporting many hormones, metabolites, and drugs as well as maintaining oncotic pressure and buffering blood pH. Albumin is therapeutically administered to replace lost fluid and restore blood volume in trauma, burn, and surgery patients.

Cohn first described the purification of albumin from human plasma through differential fractionation. See Cohn et al., *J. Am. Chem. Soc.* 68: 459-475 (1946); Cohn et al., *J. Am. Chem. Soc.* 69: 1753-1761 (1947); U.S. Pat. Nos. 2,390,074 and 2,469,193. These methods were improved by Gerlough. See U.S. Pat. Nos. 2,710,293 and 2,710,294. Such methods use cold ethanol and the manipulation of pH, ionic strength, protein concentration, and temperature to precipitate plasma proteins such as albumins.

The procedure for purifying albumin from human plasma for pharmaceutical products typically includes a viral inactivation step to reduce the risk of transmitting blood-borne viruses. These viral inactivation steps can include heat pasteurization, organic solvents, or combinations of organic solvents and detergents (e.g., tri-n-butyl phosphate and polysorbate 80). In addition, the fatty acid caprylate, or salt thereof (e.g., sodium caprylate), has been effectively used as a viral inactivation agent. See U.S. Pat. No. 4,939,176; International Patent Application Publication Nos. WO 1998/024485 and WO 2000/056768; Lundblad and Seng, Vox Sang. 60:75-81 (1991); Johnston, Jonstone, & Wu, Biologicals 31: 213-221 (2003). Further, caprylate has also been used as a stabilizing agent and as a partitioning agent in the purification of therapeutic human albumin. See U.S. Pat. Nos. 5,250,663 and 5,561,115.

Human albumin is purified from the Cohn Fraction IV-1 Effluent or Fraction V and includes an acetone drying step to concentrate the albumin and inactivate viruses. The acetone process is expensive and uses large quantities of acetone, which creates a fire or explosion hazard. Accordingly, alternative viral inactivation and concentration procedures are desirable. A method for purifying albumin from human plasma using caprylate viral inactivation under conditions of low pH and elevated temperature followed by ultrafiltration/diafiltration is described herein.

SUMMARY

Described herein are methods for inactivating viruses using caprylate during the purification of albumin from plasma.

One embodiment described herein is a method of preparing albumin from a solution comprising albumin comprising: adjusting the protein concentration of the solution to less than about 5%; adjusting pH of the solution to about pH 5 or less; adding caprylic acid (octanoic acid) or sodium caprylate; raising the solution temperature greater than about 20° C.; and incubating the solution.

In some aspects described herein, the incubation temperature is 27-30° C.

In some aspects described herein, the incubation is for about 30 min to about 120 min.

In some aspects described herein, the incubation is for at least about 90 min.

In some aspects described herein, the caprylate concentration is about 10 mM to about 40 mM.

In some aspects described herein, the caprylate concentration is about 15 mM to about 30 mM.

In some aspects described herein, the caprylate concentration is about 20 mM.

In some aspects described herein, the pH is about 3.8 to about 5.

In some aspects described herein, the pH is about 5.

In some aspects described herein, the method further comprises: filtering the solution; performing ultrafiltration and diafiltration; formulating and bulking the solution; and sterilizing, filling, and pasteurizing the albumin.

Another embodiment described herein is a method of preparing albumin from a solution comprising albumin: adjusting the protein concentration of the solution to less than about 5%; adjusting pH of the solution to about pH 5 or less; adding caprylic acid (octanoic acid) or sodium caprylate to a concentration of about 20 mM; raising the solution temperature to about 27-30° C.; and incubating the solution for at least about 30 min to about 120 min.

In some aspects described herein, the incubation is for at least about 90 min.

In some aspects described herein, the pH is about 5.

In some aspects described herein, the method further comprises: filtering the solution; performing ultrafiltration and diafiltration; formulating and bulking the solution; and sterilizing, filling, and pasteurizing the albumin.

Another embodiment described herein is a method of inactivating viruses in a solution comprising albumin, the method comprising: adjusting the protein concentration of solution to about 5% protein; adjusting pH of the solution to less than about 5; adding caprylic acid (octanoic acid) or sodium caprylate; raising the solution temperature greater than about 20° C.; and incubating the solution.

In some aspects described herein, the viruses are lipid-enveloped viruses.

In some aspects described herein, the caprylate concentration is about 15 mM to about 30 mM.

In some aspects described herein, the temperature is about 27-30° C.

In some aspects described herein, the incubation is for at least 90 min.

In some aspects described herein, the caprylate concentration is 20 mM.

In some aspects described herein, the incubation is 90 min.

In some aspects described herein, the temperature is 30° C.

In some aspects described herein, the viruses are lipid-enveloped viruses infecting humans.

Another embodiment described herein is a method of inactivating viruses in a solution comprising albumin, the method comprising: adjusting the protein concentration of solution to about 5% protein; adjusting pH of the solution to less than about 5; adding caprylic acid (octanoic acid) or sodium caprylate to a concentration of about 20 mM; raising the solution temperature to about 27-30° C.; and incubating the solution for at least 90 min.

In some aspects described herein, the viruses are lipid-enveloped viruses infecting humans.

In some aspects described herein, the method further comprises: filtering the solution; performing ultrafiltration and diafiltration; formulating and bulking the solution; and sterilizing, filling, and pasteurizing the albumin.

DETAILED DESCRIPTION

A current albumin purification process includes an acetone drying step. The acetone drying step has been validated as a virus inactivation step. However, the acetone step is difficult, requires expensive operating equipment, and the large quantities of acetone used present a flammability and/or explosion issue, which requires extensive safety precautions. Replacing the acetone drying steps is desirable. The caprylate incubation described herein can be used as a virus inactivation step and then the albumin can be concentrated using an ultrafiltration/diafiltration step.

Caprylic acid (caprylate; octanoic acid) can be an effective viral inactivation agent. Further, caprylate is currently used in the albumin formulation, and thus caprylate vial inactivation can be easily integrated into the albumin process without introducing additional reagents such as solvents or detergents and with minimal changes to the process.

Caprylic acid or sodium caprylate is added to albumin formulations as a stabilizer during the bulking step. However, the pH of the albumin solution in the bulking is too high (~7) to create enough free caprylic acid for virus inactivation. Caprylate can be added during the suspension of the Fraction V paste (albumin paste), which is already a low-pH solution. Because caprylate is essentially a stabilizer for albumin, its effect on the albumin is minimal. Proper filtration prior to UF/DF removes much of the caprylate in the form of undissolved caprylic acid. As the albumin processing continues in the UF/DF steps, the pH will be increased and the sodium caprylate will be washed out by diafiltration to allow normal bulking of the albumin.

Overall, the modified albumin process consists of using Fraction IV-1 Effluent (or filtrate) or Cohn V paste as input material. The Cohn V paste was resuspended in cold water for injection or the Fraction IV-1 Effluent was diluted to a protein concentration of approximately 25 AU ($A_{280}$). Sodium caprylate was added to a concentration of 20 mM caprylate and the pH was adjusted to less than pH 5, if necessary. The solution was then incubated at 27-30° C. for 90 min. See FIG. 7.

To test the viricidal efficacy, viral inactivation experiments were carried out with a panel of enveloped viruses (i.e., bovine viral diarrheal virus (BVDV), pseudorabies virus (PRV) and human immunodeficiency virus (HIV)) in Cohn Fraction V suspension and albumin suspension using a scaled down model of the proposed manufacturing process. Fraction V paste or albumin paste was suspended in water, spiked with about 5% virus, and the pH adjusted to the appropriate target, if necessary. Sodium caprylate was added to achieve the targeted caprylate concentration, the pH of the solution was verified, and the solution was incubated at the appropriate temperature. Samples were removed at various time points during the incubation and titrated using cell based assays to quantitate infectious virus. Rapid and effective inactivation of BVDV, PSV, and HIV were observed under the appropriate conditions of pH, caprylate concentration, protein concentration, and temperature.

Process capability was assessed separately for both Fraction V and Albumin paste suspensions using a scale down (500 g paste suspension) of the proposed manufacturing process. Sodium caprylate was added and pH was adjusted, as necessary, to achieve the targeted caprylate concentration and pH. Following incubation, the material was filtered, processed through UF/DF, formulated, bulked, sterile filtered, and pasteurized. Intermediate and final product characterization data derived from a bench-scale study modified process were comparable with those derived from a bench-scale control run and with those derived from the current full-scale manufacturing process.

Modified process bench-scale runs were conducted with Cohn Fraction V or albumin paste. Approximately 500 g of paste was initially dissolved in cold water for injection. The dissolved paste was then heated to a temperature of ~27° C. and sodium caprylate was added to a concentration of ~20 mM. This dissolved bulk solution was allowed to incubate for 90 minutes to allow viral inactivation to occur. Clarification of the albumin solution was accomplished by filtration through a series of filters. The clarified albumin solution was then concentrated to ~12% w/v by ultrafiltration, the protein bulk was diafiltered with saline solution and cold water for injection. A concentration of ~28% protein was achieved by a second ultrafiltration step. The UF/DF protein bulk solution was then formulated with additions of sodium hydroxide, tryptophan, and sodium caprylate. The formulated bulk solution was the sterile filtered, filled into vials, stoppered, and oversealed. These vials were then pasteurized at 60° C. for 10-11 hours to arrive at final container.

It was surprising to find that caprylate can function as both a viral inactivator and a stabilizer simultaneously during the process at the protein and caprylate concentrations used, and the length and temperature of the incubation. This was also surprising because albumin binds caprylate and the concentrations of caprylate were effective for viral inactivation at moderate protein concentrations with short incubations at room temperature.

The current albumin purification process, including the acetone drying step, is described in Example 1 and begins with Cohn Effluent IV-1 or Fraction V. See Cohn et al., *J. Am. Chem. Soc.* 68: 459-475 (1946); Cohn et al., *J. Am. Chem. Soc.* 69: 1753-1761 (1947); U.S. Pat. Nos. 2,390,074 and 2,469,193.

Example 1

Preparation of Human Albumin

Cohn Fraction V was suspended in cold water for injection. Alternatively, Effluent IV-1 can be used instead of Fraction V. Cold denatured ethanol (SDA-3A) was added to obtain an alcohol solution of about 10%, while cooling the solution to a temperature of about 0° C. The solution was mixed for about 1 hour at about 0° C., and then clarified by depth filtration.

The albumin fraction was then precipitated from Effluent IV-1 or Fraction V by adjusting the pH, adding cold denatured ethanol (SDA-3A), and incubating the solution at low temperature. After the low temperature incubation, the albumin fraction was separated by centrifugation.

Acetone Viral Inactivation

The albumin fraction was then suspended in cold acetone and held for approximately minutes at about 0° C. The protein was separated from the slurry and rinsed with cold acetone. The moist albumin powder was dried by passing dry nitrogen and/or air through the powder.

Concentration and Filtration

The dried albumin powder was dissolved in cold water for injection to a protein concentration of about 7%. The albumin solution was clarified by filtration through a series of filters graduated in porosity to a final 0.2 µm absolute filter (diatomite was used as necessary to aid filtration). The pH of the albumin solution was adjusted to about pH 7, ultrafiltered to concentrate the solution approximately two-fold, and then diafiltered with 3% NaCl followed by water for injection. The albumin solution was then concentrated, if necessary, by ultrafiltration to the appropriate protein concentration (ca. 25%).

Bulking, Sterilization, Filling, and Pasteurization

Aqueous bulk of albumin was prepared by adjusting the ultrafiltered/diafiltered albumin solution with sodium caprylate, excipients, sodium hydroxide, sodium chloride, and water for injection to achieve 20 mM sodium caprylate, 25% protein, and pH 7. The pH was adjusted with 1.0 M sodium carbonate and/or 1.0 M HCl, if necessary.

The albumin solution was sterilized by filtration through a series of filters graduated in porosity to a final 0.2 µm absolute filter. The sterile albumin solution was aseptically filled into sterile bottles and pasteurized for about 10 hours at about 60° C. The final containers were incubated at 25° C. for about two weeks and then stored at room temperature.

Example 2

Virus Inactivation Experiments

Figure 1:
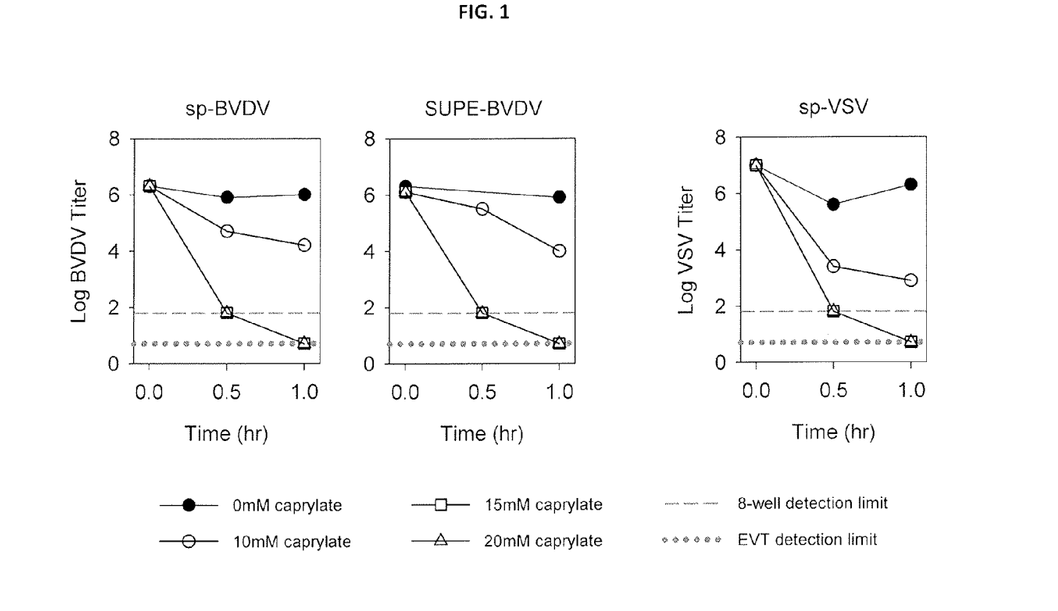
FIG. 1 illustrates results from caprylate-induced virus inactivation in 25 AU albumin paste suspensions at 27° C., pH 5.1 over 1 hour. Caprylate concentrations of 0, 10, 15, and 20 mM were assessed at 0, 0.5, and 1-hour intervals. The results show that 15 mM caprylate effectively inactivates bovine viral diarrhea virus and vesicular stomatitis virus to the limit of detection within 1 hour at 27° C.

Acetone treatment of albumin paste is a very effective enveloped virus inactivation step but is a bottleneck in the process and is associated with numerous cleaning and safety issues (fire hazards). Consequently, caprylate treatment is a possible alternative to acetone suspension and drying. Experiments were performed to evaluate enveloped virus inactivation by caprylate treatment of albumin paste suspension. For the studies, albumin paste suspension with a protein concentration of 25 AU was spiked with bovine viral diarrhea virus (BVDV) or vesicular stomatitis virus (VSV) and incubated for 1 hr at 27° C., pH 5.1, with 0, 10, 15, or 20 mM caprylate. Data show virus inactivation to the limit of detection after treatment with 15 mM caprylate. See Table 1 and FIG. 1.

TABLE 1

Viral Inactivation Experiments

| | Log Virus Titer | | | | | | | | | | | |
|---|---|---|---|---|---|---|---|---|---|---|---|---|
| | SP-BVDV | | | | SUPE-BVDV | | | | SP-VSV | | | |
| t (hr) | A 0 mM | B 10 mM | C 15 mM | D 20 mM | E 0 mM | F 10 mM | G 15 mM | H 20 mM | I 0 mM | J 10 mM | K 15 mM | L 20 mM |
| 0.0 | 6.3 | 6.3 | 6.3 | 5.1 | 6.3 | 6.1 | 6.1 | 5.2 | 7.0 | 6.6 | 6.4 | 5.6 |
| 0.5 | 5.9 | 4.7 | 1.8 | 1.8 | | 5.5 | 1.8 | 1.8 | 5.6 | 3.4 | 1.8 | 1.8 |
| 1.0 | 6.0 | 4.2 | 0.7* | 0.7* | 5.9 | 4.0 | 0.7* | 0.7* | 6.3 | 2.9 | 0.7* | 0.7* |
| LRV | 0.3 | 2.1 | ≥5.6 | ≥5.6 | 0.4 | 2.1 | ≥5.4 | ≥5.4 | 0.7 | 4.1 | ≥6.3 | ≥6.3 |

*Extended volume testing; underlined values = no detectable virus

Example 3

Experiments were conducted to evaluate the virucidal capacity of caprylate at low temperatures. Albumin and Fraction V paste suspensions were diluted to 25 and 65 absorbance units (AU), and sodium caprylate was added to a final concentration of 20 mM. The solutions were adjusted to pH 4.5 or 5.1 and spiked with pH-adjusted BVDV before incubation at 5, 12, or 20° C. Samples for titration, pH, and/or protein concentration (i.e., $A_{280}$) were removed after spiking (0 hour) and at 0.5, 2, and 6 hours.

Figure 2:
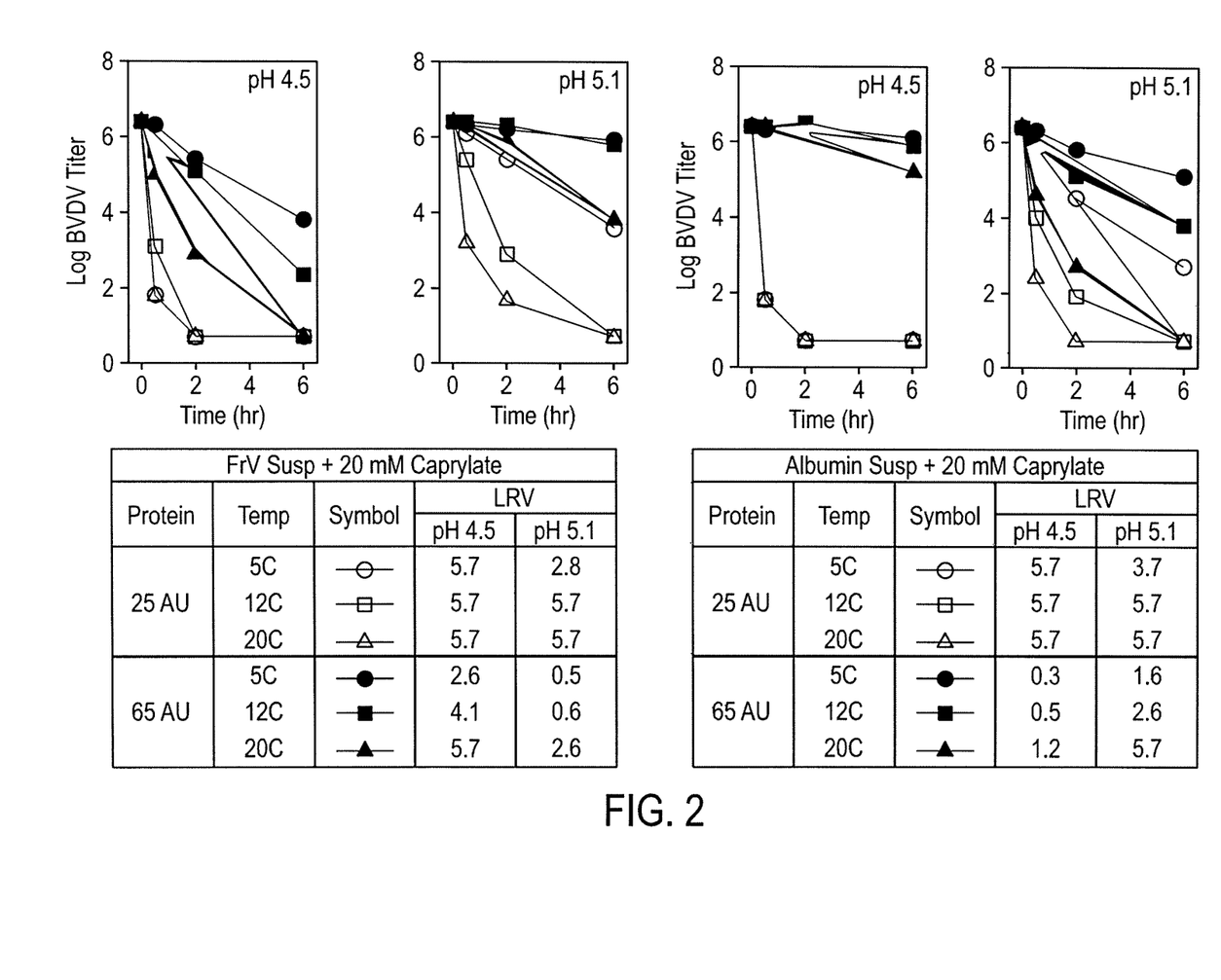
FIG. 2 illustrates results from 20 mM caprylate-induced virus inactivation at 25 or 65 AU albumin concentrations, at either pH 4.5 or 5.1 at three, low temperatures, 5, 12, and 20° C. over a 6-hour period. The results show that at lower concentrations of albumin, 20 mM caprylate was effective as a viral inactivator at 20° C. after 2 hours. However, viral inactivation was not robust under lower temperatures and was dependent on pH, incubation time, and albumin concentration.
Figure 3:
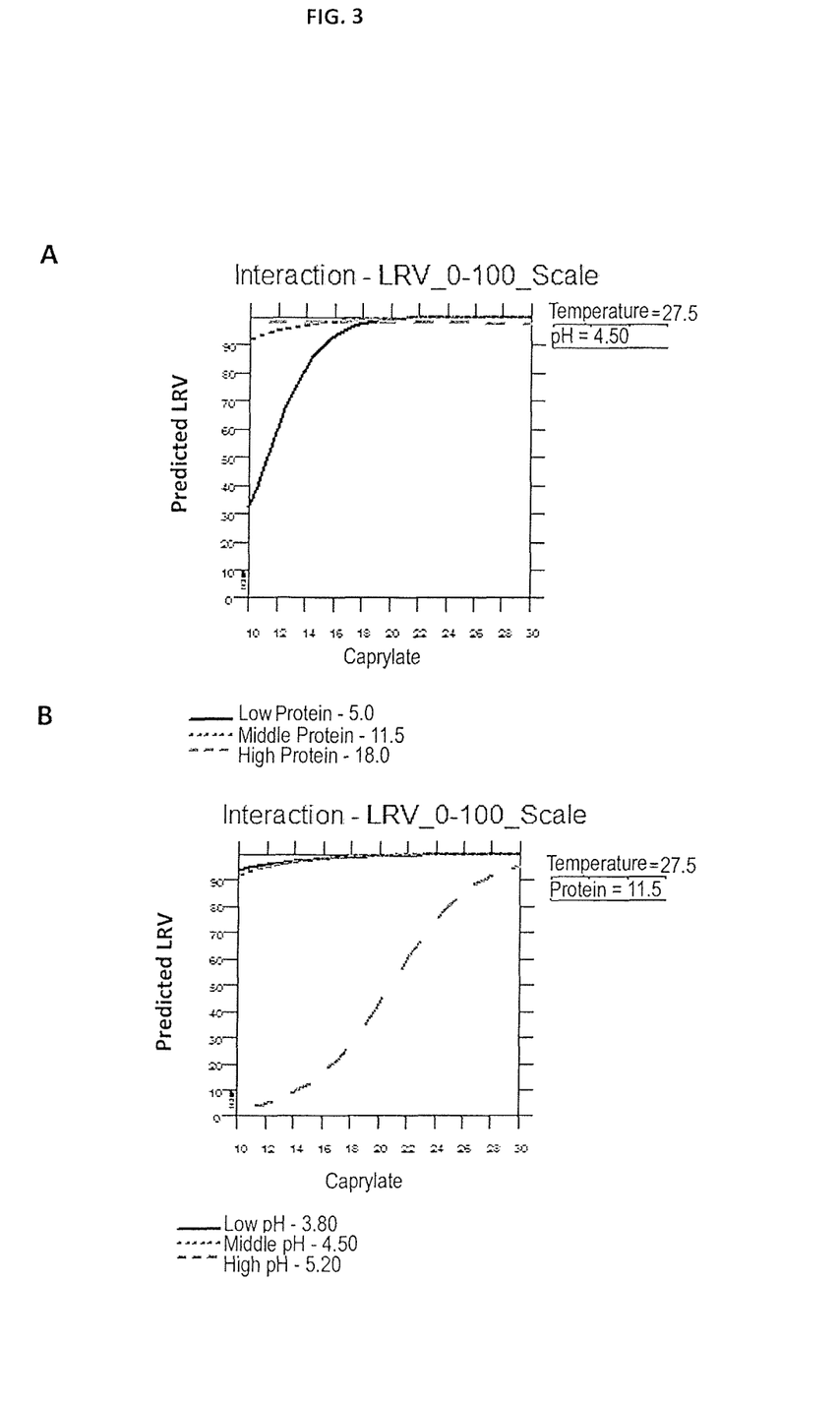
FIG. 3 illustrates design of experiment (DOE) responses and predicted log reduction values (LRV) for protein concentration as a function of caprylate concentration (Panel A) at constant temperature (27.5° C.) and pH (4.5). Panel B shows responses and predicted LRV for pH as a function of caprylate concentration at constant temperature (27.5° C.) and protein concentration (11.5%)
Figure 4:
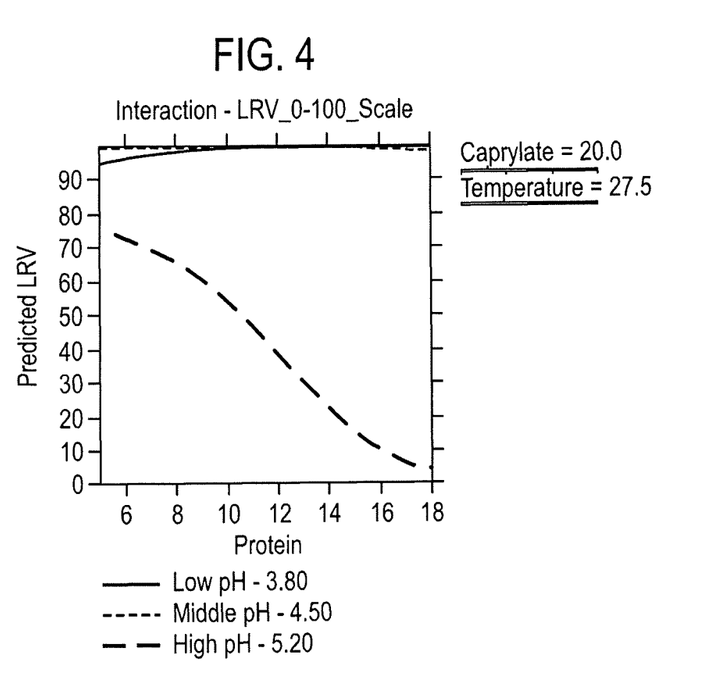
FIG. 4 illustrates DOE responses and predicted LRV for pH as a function of protein concentration at constant temperature (27.5° C.) and caprylate concentration (20 mM).
Figure 5A:
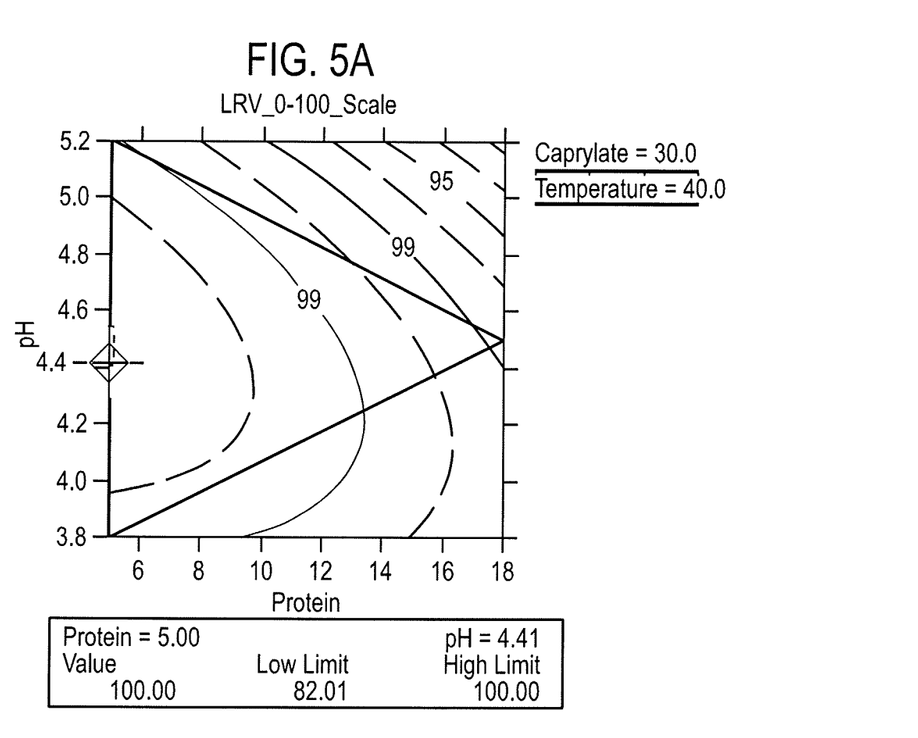
FIG. 5 shows a contour graph representing the response surface for LRV at the 95 and greater confidence intervals for pH as a function of protein concentration at 30 mM caprylate and 40° C. (Panel A). Panel B shows a three-dimensional representation of the response surface. LRV was maximized (i.e., 100%) with the smallest 95% prediction interval with conditions of pH 4.4 and protein concentration of 5%, at 30 mM caprylate and 40° C.
Figure 5B:
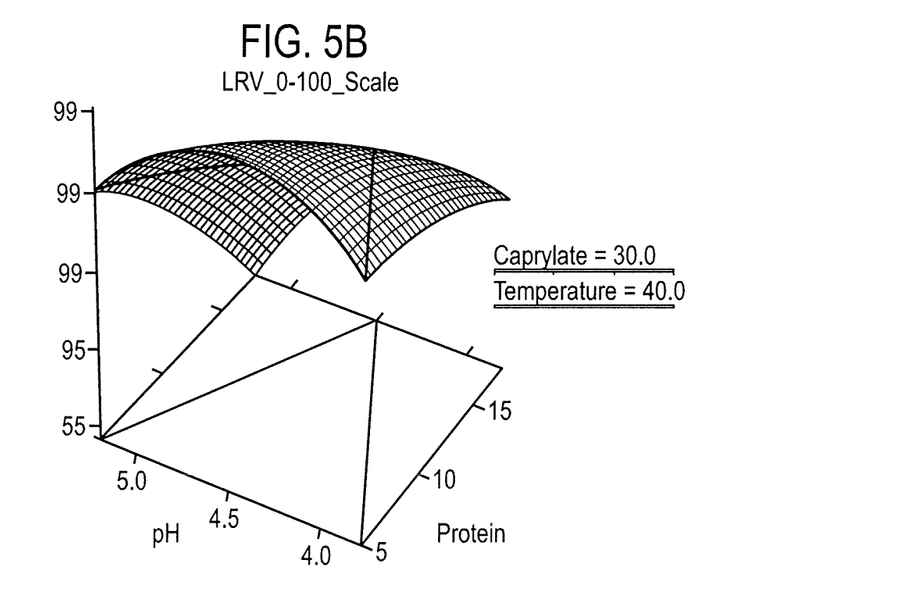

For both Albumin and Fraction V paste suspensions, virus inactivation by caprylate was greater at higher temperatures and at lower protein concentrations. See FIG. 2. For 25 AU and 65 AU Fraction V suspensions, virus inactivation was higher at pH 4.5 than at pH 5.1. Virus inactivation was also higher at pH 4.5 for albumin suspensions at 25 AU. For albumin suspensions at 65 AU, however, virus inactivation was greater at pH 5.1 than at pH 4.5. Because the mechanism of virus inactivation by caprylate is attributed to the non-ionized form of caprylate, and the concentrations of the non-ionized form should be higher at pH 4.5 than at pH 5.1, the results with 65 AU albumin were unexpected.

Virus inactivation is dependent on pH, exposure time, protein concentration, and product composition. Unlike treatment at 27° C., which inactivated BVDV to below detection within 30 minutes (data not shown), treatment at 5° C. under optimal conditions (25 AU, pH 4.5) required 2 hours for complete BVDV inactivation. A 5° C. albumin/Fraction V caprylate incubation step was not effective for enveloped virus inactivation.

Example 4

Design of Experiment Study of Viral Inactivation Process Variables

Based on the initial results with caprylate virus inactivation in albumin or Fraction V samples, a Design of Experiment study was undertaken to evaluate conditions that would maximize viricidal activity. The variables that were optimized were Albumin Concentration (5% to 20%); caprylate concentration (10 mM to 30 mM); solution pH (3.8 to 5.5); incubation temperature (20° C. to 40° C.); and incubation time (10 min and 120 min). The response variables were the log of virus reduction value (LRV), albumin concentration, aggregation (% monomer) and haptoglobulin concentration. A linear Design of Experiment was designed to test three levels of each variable (i.e., Low, Middle, and High; see Table 2).

TABLE 2

Design of Experiment Variables

| Variable | Variable Level | Initial Parameters | Final Parameters |
| --- | --- | --- | --- |
| Albumin Concentration (±1 AU) | Low | 26.5 AU (5%) | 26.5 AU (5%) |
|  | Middle | 66.25 AU (12.5%) | 60.95 AU (11.5%) |
|  | High | 106 AU (20%) | 95.4 AU (18%) |
| Caprylate Concentration | Low | 3 mM | 10 mM |
|  | Middle | 16.5 mM | 20 mM |
|  | High | 30 mM | 30 mM |
| Temperature (±1° C.) | Low | 20° C. | 15° C. |
|  | Middle | 30° C. | 27.5° C. |
|  | High | 40° C. | 40° C. |
| pH (±1) | Low | 3.8 | 3.8 |
|  | Middle | 4.65 | 4.50 |
|  | High | 5.50 | 5.20 |

A total of 28 individual experiments were performed. See Table 3.

TABLE 3

Design of Experiment Trials

| Day | Trial | Caprylate Conc. (mM) | Temperature (C.) | Protein Conc. (%) | pH |
| --- | --- | --- | --- | --- | --- |
| 1 | 1a | 10 | 15 | 5 | 3.8 |
|  | 17 | 20 | 40 | 5 | 3.8 |
|  | 20 | 10 | 27.5 | 5 | 5.2 |
|  | 13 | 20 | 27.5 | 18 | 5.2 |
|  | 3a | 30 | 15 | 18 | 3.8 |
| 2 | 4a | 10 | 40 | 18 | 3.8 |
|  | 7 | 30 | 15 | 18 | 5.2 |
|  | 19 | 10 | 27.5 | 18 | 3.8 |
|  | 5a | 10 | 15 | 5 | 5.2 |
|  | 6 | 30 | 40 | 5 | 5.2 |
| 3 | 14 | 30 | 27.5 | 11.5 | 5.2 |
|  | 15 | 20 | 40 | 11.5 | 5.2 |
|  | 18 | 30 | 15 | 11.5 | 3.8 |
|  | 2a | 30 | 40 | 5 | 3.8 |
|  | 5b | 10 | 15 | 5 | 5.2 |
| 4 | 11 | 10 | 40 | 5 | 4.5 |
|  | 10 | 30 | 15 | 5 | 4.5 |
|  | 3b | 30 | 15 | 18 | 3.8 |
|  | 8 | 10 | 40 | 18 | 5.2 |
|  | 4b | 10 | 40 | 18 | 3.8 |
| 5 | 9 | 30 | 40 | 18 | 4.5 |
|  | 12 | 10 | 15 | 18 | 4.5 |
|  | 16 | 20 | 15 | 5 | 5.2 |
|  | 1b | 10 | 15 | 5 | 3.8 |
|  | 2b | 30 | 40 | 5 | 3.8 |
|  | 4a | 10 | 40 | 18 | 3.8 |
| 6 | 4b | 10 | 40 | 18 | 3.8 |
|  | 19 | 10 | 27.5 | 18 | 3.8 |
|  | 4a | 10 | 40 | 18 | 3.8 |

Experiments were conducted as follows: Fraction V paste was suspended in water for injection and held at 2 to 8° C. overnight. The temperature was then raised to 27 to 30° C. and the concentration (based on Absorbance at 280 nm) was adjusted to one of the three experimental values, e.g., 5, 11.5, or 18% (i.e., g albumin/100 mL; 26.5, 60.95, or 95.4 AU respectively; ~0.75 M, 1.7 M, or 2.7 M, respectively). Afterwards, the pH of the solution was adjusted (pH 3.8, 4.5, or 5.2). The samples were then incubated at the experimental temperature (e.g., 15, 27.5, or 40° C. Virus was then added at a concentration of 1%. Caprylate was then added at one of three concentrations: 10, 20, or 30 mM. The samples were then incubated at the experimental temperature for 120 min. Titration samples (prior to caprylate addition and at 5, 10, 15, 30, 60, 90, and 120 min) were also obtained to determine the kinetics of the caprylate viricidal activity. Finally, the LRV was determined for each experiment. Experimental results are shown in Table 4 and FIGS. 3-6.

TABLE 4

Design of Experiment Results

| Day | Trial | Caprylate Conc. (mM) | Temperature (C) | Protein Conc. (%) | pH | LRV, 10 min | LRV, 120 min |
|---|---|---|---|---|---|---|---|
| 1 | 1a | 10 | 15 | 5 | 3.8 | <0.2 LRV | >1.8 LRV |
|   | 17 | 20 | 40 | 5 | 3.8 | >1.8 LRV | >1.8 LRV |
|   | 20 | 10 | 27.5 | 5 | 5.2 | >1.8 LRV | <0.2 LRV |
|   | 13 | 20 | 27.5 | 18 | 5.2 | >1.8 LRV | 0.2 < LRV < 1.8 |
|   | 3a | 30 | 15 | 18 | 3.8 | 0.2 < LRV < 1.8 | >1.8 LRV |
| 2 | 4a | 10 | 40 | 18 | 3.8 | —* | >1.8 LRV |
|   | 7 | 30 | 15 | 18 | 5.2 | 0.2 < LRV < 1.8 | 0.2 < LRV < 1.8 |
|   | 19 | 10 | 27.5 | 18 | 3.8 | —* | —* |
|   | 5a | 10 | 15 | 5 | 5.2 | 0.2 < LRV < 1.8 | 0.2 < LRV < 1.8 |
|   | 6 | 30 | 40 | 5 | 5.2 | >1.8 LRV | >1.8 LRV |
| 3 | 14 | 30 | 27.5 | 11.5 | 5.2 | 0.2 < LRV < 1.8 | >1.8 LRV |
|   | 15 | 20 | 40 | 11.5 | 5.2 | 0.2 < LRV < 1.8 | >1.8 LRV |
|   | 18 | 30 | 15 | 11.5 | 3.8 | >1.8 LRV | >1.8 LRV |
|   | 2a | 30 | 40 | 5 | 3.8 | >1.8 LRV | >1.8 LRV |
|   | 5b | 10 | 15 | 5 | 5.2 | 0.2 < LRV < 1.8 | <0.2 LRV |
| 4 | 11 | 10 | 40 | 5 | 4.5 | 0.2 < LRV < 1.8 | >1.8 LRV |
|   | 10 | 30 | 15 | 5 | 4.5 | >1.8 LRV | >1.8 LRV |
|   | 3b | 30 | 15 | 18 | 3.8 | 0.2 < LRV < 1.8 | >1.8 LRV |
|   | 8 | 10 | 40 | 18 | 5.2 | 0.2 < LRV < 1.8 | 0.2 < LRV < 1.8 |
|   | 4b | 10 | 40 | 18 | 3.8 | —* | —* |
| 5 | 9 | 30 | 40 | 18 | 4.5 | >1.8 LRV | >1.8 LRV |
|   | 12 | 10 | 15 | 18 | 4.5 | 0.2 < LRV < 1.8 | 0.2 < LRV < 1.8 |
|   | 16 | 20 | 15 | 5 | 5.2 | 0.2 < LRV < 1.8 | 0.2 < LRV < 1.8 |
|   | 1b | 10 | 15 | 5 | 3.8 | 0.2 < LRV < 1.8 | >1.8 LRV |
|   | 2b | 30 | 40 | 5 | 3.8 | >1.8 LRV | >1.8 LRV |
|   | 4a | 10 | 40 | 18 | 3.8 | —* | —* |
| 6 | 4b | 10 | 40 | 18 | 3.8 | >1.8 LRV | >1.8 LRV |
|   | 19 | 10 | 27.5 | 18 | 3.8 | >1.8 LRV | >1.8 LRV |
|   | 4a | 10 | 40 | 18 | 3.8 | >1.8 LRV | >1.8 LRV |

—* These reaction gelled and no data was obtained.
Cell shading corresponds to: >1.8 LRV effective viricidal activity; 0.2 < LRV < 1.8 some viricidal activity; <0.2 LRV limited viricidal activity.

There were an array of caprylate concentrations, protein concentrations, temperatures, and pHs that were effective in viricidal activity. Based on the conditions tested in the DOE study, the following generalities were apparent:

Increased temperature enhances viricidal activity;
Increased incubation time enhances viricidal activity;
Increased caprylate concentration enhances viricidal activity;
Decreased protein concentration (albumin) enhances viricidal activity; and
Decreased pH enhances viricidal activity.

Figure 6A:
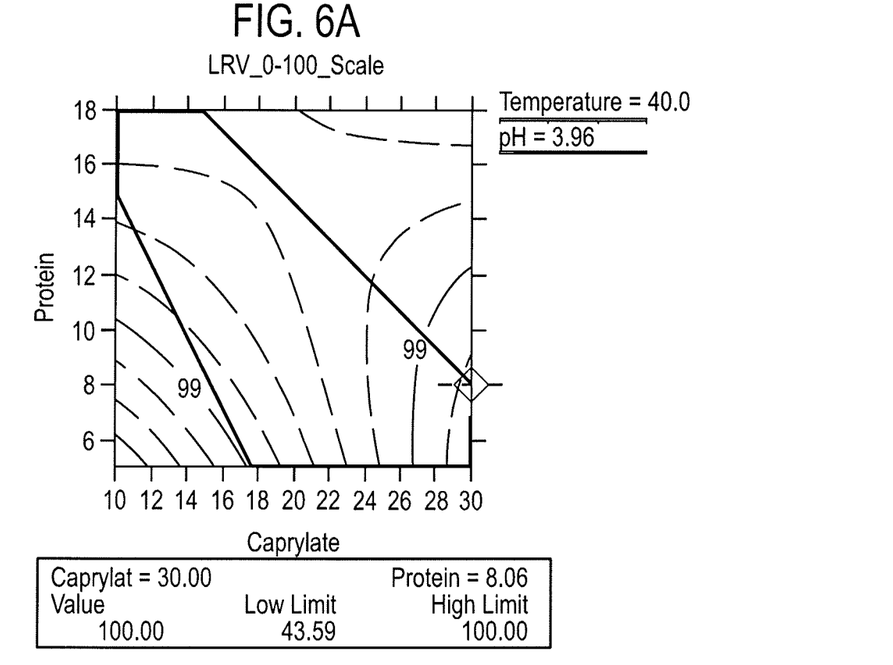
FIG. 6 shows contour graphs representing the response surface for LRV at the 95 and greater confidence intervals for protein concentration as a function of caprylate concentration at pH 3.96 and 40° C. (Panel A) or pH as a function of caprylate concentration at 6.6% protein and 36.9° C. (Panel B).
Figure 6B:
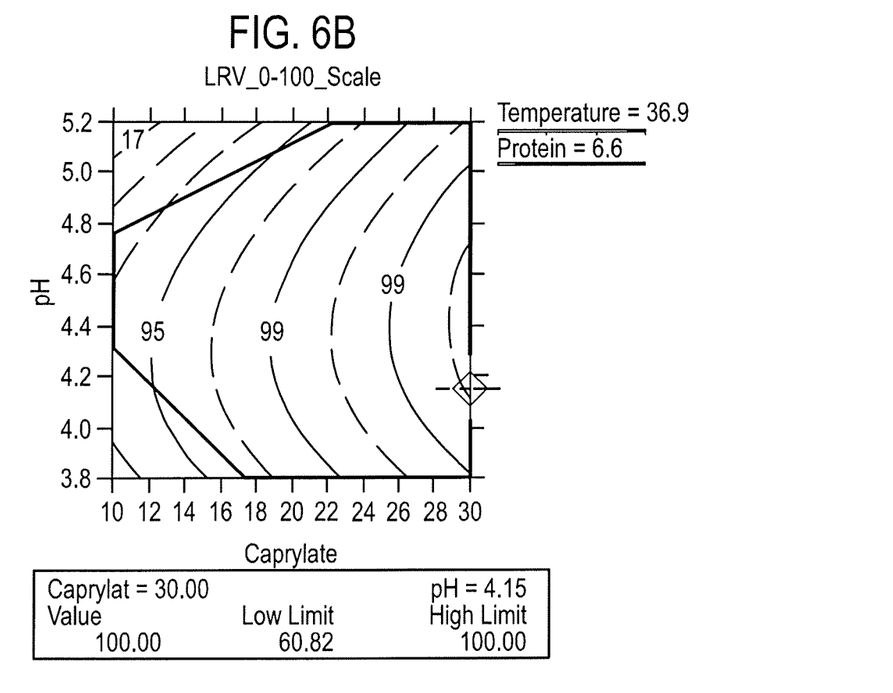
Figure 7:
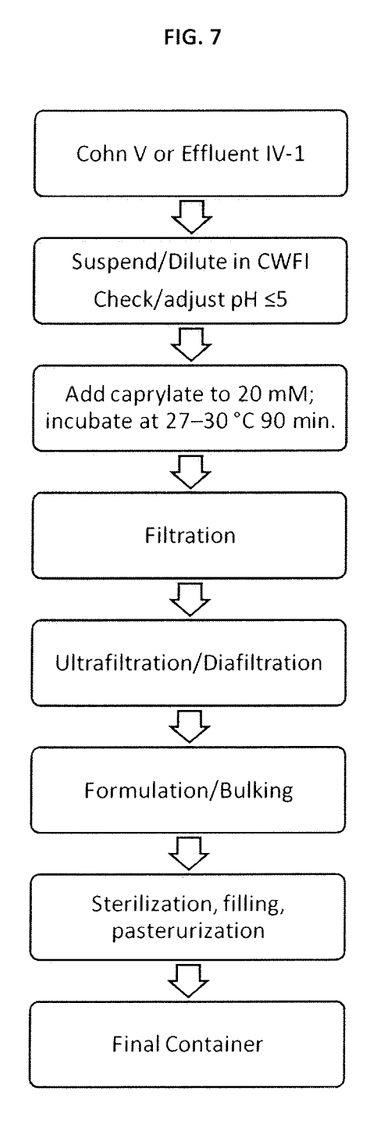
FIG. 7 shows a flow chart of the modified albumin purification process including a caprylate viral inactivation step.

Furthermore, the predicted LRV on the 0 to 100 scale is maximized, i.e., equal to 100% (the equivalent to an LRV of 2.16), with the smallest 95% confidence prediction interval at the following joint variable settings (see FIGS. 6-7):

Caprylate Concentration: 30 mM;
Albumin concentration: 5% (ca. 26.5 AU; 750 mM);
pH: 4.4;
Temperature: 40° C.; and
Incubation time: 120 min.

Based on these data, the following conditions were determined as practical for a virus inactivation step in the albumin purification process:

Protein concentration: ≤25 AU ($A_{280}$) (i.e., <5%; <750 mM)
Caprylate concentration: ≥20 mM;
pH: ≤5.0;
Temperature: 27-30° C.; and
Incubation time: ≥90 min.

These conditions maximize viricidal activity while reducing manufacturing cost and time in the albumin purification process.

The scope of the conditions, methods, and processes described herein includes all combinations of embodiments, aspects, examples, steps, and preferences herein described.

What is claimed is:

1. A method of preparing albumin from a solution comprising albumin, the method comprising:
   (i) adjusting the protein concentration of the solution to less than about 5%;
   (ii) adding caprylic acid (octanoic acid) or sodium caprylate to the solution obtained in step (i);
   (iii) adjusting pH of the solution obtained in step (ii) to about pH 5 or less;
   (iv) raising the temperature of the solution obtained in step (iii) to about 27-30° C.; and
   (v) incubating the solution obtained in step (iv) for about 30 min to 120 min.

2. The method of claim 1, wherein the incubation is for at least about 90 min.

3. The method of claim 1, wherein the caprylate concentration is about 10 mM to about 40 mM.

4. The method of claim 1, wherein the caprylate concentration is about 15 mM to about 30 mM.

5. The method of claim 1, wherein the caprylate concentration is about 20 mM.

6. The method of claim 1, wherein the pH is about 3.8 to about 5.

7. The method of claim 1, wherein the pH is about 5.

8. The method of claim 1, further comprising:
   filtering the solution;
   performing ultrafiltration and diafiltration;
   formulating and bulking the solution; and
   sterilizing, filling, and pasteurizing the albumin.

9. A method of preparing albumin from a solution comprising albumin, the method comprising:
   (i) adjusting the protein concentration of the solution to less than about 5%;
   (ii) adding caprylic acid (octanoic acid) or sodium caprylate to a concentration of about 20 mM to the solution obtained in step (i);

(iii) adjusting pH of the solution obtained in step (ii) to about pH 5 or less;
(iv) raising the temperature of the solution obtained in step (iii) to about 27-30° C.; and
(v) incubating the solution obtained in step (iv) for at least about 30 min to about 120 min.

10. The method of claim 9, wherein the incubation is for at least about 90 min.

11. The method of claim 9, wherein the pH is about 5.

12. The method of claim 9, further comprising:
filtering the solution;
performing ultrafiltration and diafiltration;
formulating and bulking the solution; and
sterilizing, filling, and pasteurizing the albumin.

13. A method of inactivating viruses in a solution comprising albumin, the method comprising:
(i) adjusting the protein concentration of the solution to less than about 5%;
(ii) adding caprylic acid (octanoic acid) or sodium caprylate to the solution obtained in step (i), wherein the caprylic acid or sodium caprylate concentration is greater than about 20 mM;
(iii) raising the solution temperature of the solution obtained in step (ii) to greater than about 20° C.;
iv) incubating the solution;
v) filtering the solution;
vi) performing ultrafiltration and diafiltration;
vii) formulating and bulking the solution; and
viii) sterilizing, filling, and pasteurizing the albumin.

14. The method of claim 13, wherein the viruses are lipid-enveloped viruses.

15. The method of claim 13, wherein the temperature is about 27-30° C.

16. The method of claim 13, wherein the incubation is for at least 90 min.

17. The method of claim 13, wherein the incubation is 90 min.

18. The method of claim 13, wherein the temperature is 30° C.

19. The method of claim 14, wherein the viruses are lipid-enveloped viruses infecting humans.

20. A method of inactivating viruses in a solution comprising albumin, the method comprising:
(i) adjusting the protein concentration of the solution to less than about 5%;
(ii) adding caprylic acid (octanoic acid) or sodium caprylate to a concentration of about 20 mM to the solution obtained in step (i);
(iii) raising the temperature of the solution obtained in step (ii) to about 27-30° C.;
(iv) incubating the solution for at least 90 min;
(v) filtering the solution;
(vi) performing ultrafiltration and diafiltration;
(vii) formulating and bulking the solution; and
(viii) sterilizing, filling, and pasteurizing the albumin.

21. The method of claim 20, wherein the viruses are lipid-enveloped viruses infecting humans.

* * * * *